United States Patent
Venkatasubramanian

(10) Patent No.: US 9,801,721 B2
(45) Date of Patent: Oct. 31, 2017

(54) SIZING DEVICE AND METHOD OF POSITIONING A PROSTHETIC HEART VALVE

(71) Applicant: St. Jude Medical, Cardiology Division, Inc., St. Paul, MN (US)

(72) Inventor: Ramji T. Venkatasubramanian, Maplewood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 223 days.

(21) Appl. No.: 13/788,631

(22) Filed: Mar. 7, 2013

(65) Prior Publication Data
US 2014/0107768 A1    Apr. 17, 2014

Related U.S. Application Data

(60) Provisional application No. 61/713,171, filed on Oct. 12, 2012.

(51) Int. Cl.
| | | |
|---|---|---|
| A61F 2/24 | (2006.01) |
| A61B 5/00 | (2006.01) |
| A61B 5/107 | (2006.01) |

(52) U.S. Cl.
CPC .......... *A61F 2/2496* (2013.01); *A61B 5/1076* (2013.01); *A61B 5/6862* (2013.01); *A61B 5/6869* (2013.01); *A61F 2/2418* (2013.01); *A61F 2230/001* (2013.01)

(58) Field of Classification Search
USPC ................................. 600/587; 623/2.11–2.18
See application file for complete search history.

(56) References Cited

U.S. PATENT DOCUMENTS

| | | | |
|---|---|---|---|
| 3,657,744 A * | 4/1972 | Ersek ........................... 128/898 |
| 4,275,469 A | 6/1981 | Gabbay |
| 4,491,986 A | 1/1985 | Gabbay |
| 4,759,758 A | 7/1988 | Gabbay |
| 4,856,529 A * | 8/1989 | Segal ............................ 600/454 |
| 4,878,906 A | 11/1989 | Lindemann et al. |
| 4,922,905 A | 5/1990 | Strecker |
| 4,994,077 A | 2/1991 | Dobben |
| 5,156,157 A * | 10/1992 | Valenta et al. ................ 600/463 |
| 5,411,552 A | 5/1995 | Andersen et al. |
| 5,480,423 A | 1/1996 | Ravenscroft et al. |
| 5,785,657 A * | 7/1998 | Breyer et al. ................. 600/454 |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report and Written Opinion for Application No. PCT/US2013/064198 dated Jan. 21, 2014.

(Continued)

*Primary Examiner* — Sean Dougherty
(74) *Attorney, Agent, or Firm* — Lerner, David, Littenberg, Krumholz & Mentlik, LLP

(57) ABSTRACT

A sizing device for a collapsible prosthetic heart valve includes a collapsible and expandable stent. A microelectromechanical sensor is coupled to the stent, the sensor being capable of collecting information related to the size and stiffness of tissue.

21 Claims, 9 Drawing Sheets

(56) References Cited

U.S. PATENT DOCUMENTS

| | | | | |
|---|---|---|---|---|
| 5,843,167 | A | 12/1998 | Dwyer et al. | |
| 5,855,601 | A | 1/1999 | Bessler et al. | |
| 5,935,163 | A | 8/1999 | Gabbay | |
| 5,961,549 | A | 10/1999 | Nguyen et al. | |
| 6,053,873 | A * | 4/2000 | Govari | A61B 5/0031 600/462 |
| 6,077,297 | A | 6/2000 | Robinson et al. | |
| 6,083,257 | A | 7/2000 | Taylor et al. | |
| 6,090,140 | A | 7/2000 | Gabbay | |
| 6,162,246 | A * | 12/2000 | Barone | A61F 2/07 623/1.1 |
| 6,197,047 | B1 * | 3/2001 | Kranz | A61F 2/91 623/1.1 |
| 6,214,036 | B1 | 4/2001 | Letendre et al. | |
| 6,264,691 | B1 | 7/2001 | Gabbay | |
| 6,267,783 | B1 | 7/2001 | Letendre et al. | |
| 6,368,348 | B1 | 4/2002 | Gabbay | |
| 6,398,734 | B1 * | 6/2002 | Cimochowski et al. | 600/454 |
| 6,419,695 | B1 | 7/2002 | Gabbay | |
| 6,442,413 | B1 * | 8/2002 | Silver | A61B 5/0031 600/345 |
| 6,468,660 | B2 * | 10/2002 | Ogle et al. | 428/413 |
| 6,488,702 | B1 | 12/2002 | Besselink | |
| 6,517,576 | B2 | 2/2003 | Gabbay | |
| 6,533,810 | B2 | 3/2003 | Hankh et al. | |
| 6,582,464 | B2 | 6/2003 | Gabbay | |
| 6,610,088 | B1 | 8/2003 | Gabbay | |
| 6,623,518 | B2 | 9/2003 | Thompson et al. | |
| 6,685,625 | B2 * | 2/2004 | Gabbay | 600/36 |
| 6,719,789 | B2 | 4/2004 | Cox | |
| 6,730,118 | B2 | 5/2004 | Spenser et al. | |
| 6,783,556 | B1 | 8/2004 | Gabbay | |
| 6,790,230 | B2 | 9/2004 | Beyersdorf et al. | |
| 6,814,746 | B2 | 11/2004 | Thompson et al. | |
| 6,830,584 | B1 | 12/2004 | Seguin | |
| 6,869,444 | B2 | 3/2005 | Gabbay | |
| 6,893,460 | B2 | 5/2005 | Spenser et al. | |
| 6,908,481 | B2 | 6/2005 | Cribier | |
| 7,006,858 | B2 * | 2/2006 | Silver | A61B 5/0031 600/345 |
| 7,018,406 | B2 | 3/2006 | Seguin et al. | |
| 7,025,780 | B2 | 4/2006 | Gabbay | |
| 7,137,184 | B2 * | 11/2006 | Schreck | 29/447 |
| 7,160,322 | B2 | 1/2007 | Gabbay | |
| 7,181,261 | B2 * | 2/2007 | Silver | A61B 5/0031 204/403.01 |
| 7,247,167 | B2 | 7/2007 | Gabbay | |
| 7,267,686 | B2 | 9/2007 | DiMatteo et al. | |
| 7,274,965 | B1 * | 9/2007 | Karicherla et al. | 607/119 |
| 7,311,730 | B2 | 12/2007 | Gabbay | |
| 7,329,278 | B2 | 2/2008 | Seguin et al. | |
| 7,340,288 | B1 * | 3/2008 | Karicherla et al. | 600/374 |
| 7,374,573 | B2 | 5/2008 | Gabbay | |
| 7,381,218 | B2 | 6/2008 | Schreck | |
| 7,389,134 | B1 * | 6/2008 | Karicherla et al. | 600/375 |
| 7,427,265 | B1 * | 9/2008 | Keilman | A61B 5/0031 600/300 |
| 7,448,999 | B1 * | 11/2008 | Karicherla et al. | 600/486 |
| 7,450,999 | B1 * | 11/2008 | Karicherla et al. | 607/126 |
| 7,452,371 | B2 | 11/2008 | Pavcnik et al. | |
| 7,454,244 | B2 * | 11/2008 | Kassab et al. | 600/547 |
| 7,510,572 | B2 | 3/2009 | Gabbay | |
| 7,524,331 | B2 | 4/2009 | Birdsall | |
| RE40,816 | E | 6/2009 | Taylor et al. | |
| 7,585,321 | B2 | 9/2009 | Cribier | |
| 7,682,390 | B2 | 3/2010 | Seguin | |
| 7,731,742 | B2 | 6/2010 | Schlick et al. | |
| 7,769,420 | B2 * | 8/2010 | Silver | A61B 5/0031 600/300 |
| 7,803,185 | B2 | 9/2010 | Gabbay | |
| 7,846,203 | B2 | 12/2010 | Cribier | |
| 7,846,204 | B2 | 12/2010 | Letac et al. | |
| 7,914,569 | B2 | 3/2011 | Nguyen et al. | |
| 7,951,111 | B2 * | 5/2011 | Drasler et al. | 604/103.13 |
| D648,854 | S | 11/2011 | Braido | |
| D652,926 | S | 1/2012 | Braido | |
| D652,927 | S | 1/2012 | Braido et al. | |
| D653,341 | S | 1/2012 | Braido et al. | |
| D653,342 | S | 1/2012 | Braido et al. | |
| D653,343 | S | 1/2012 | Ness et al. | |
| D654,169 | S | 2/2012 | Braido | |
| D654,170 | S | 2/2012 | Braido et al. | |
| 8,114,350 | B1 * | 2/2012 | Silver et al. | 422/68.1 |
| D660,432 | S | 5/2012 | Braido | |
| D660,433 | S | 5/2012 | Braido et al. | |
| D660,967 | S | 5/2012 | Braido et al. | |
| 8,212,552 | B2 * | 7/2012 | Gianchandani et al. | 324/228 |
| 8,406,867 | B2 * | 3/2013 | Kassab | 600/547 |
| D684,692 | S | 6/2013 | Braido | |
| 8,512,219 | B2 * | 8/2013 | Ferren | A61B 1/00156 600/101 |
| 8,550,206 | B2 * | 10/2013 | Keady et al. | 181/135 |
| 8,715,207 | B2 * | 5/2014 | Righini et al. | 600/587 |
| 2002/0036220 | A1 * | 3/2002 | Gabbay | 224/191 |
| 2003/0023303 | A1 | 1/2003 | Palmaz et al. | |
| 2003/0050694 | A1 | 3/2003 | Yang et al. | |
| 2003/0130726 | A1 | 7/2003 | Thorpe et al. | |
| 2004/0049262 | A1 | 3/2004 | Obermiller et al. | |
| 2004/0093075 | A1 | 5/2004 | Kuehne | |
| 2004/0210304 | A1 | 10/2004 | Seguin et al. | |
| 2005/0096726 | A1 | 5/2005 | Sequin et al. | |
| 2005/0137695 | A1 | 6/2005 | Salahieh et al. | |
| 2005/0137697 | A1 | 6/2005 | Salahieh et al. | |
| 2005/0256566 | A1 | 11/2005 | Gabbay | |
| 2005/0288596 | A1 * | 12/2005 | Eigler et al. | 600/485 |
| 2006/0008497 | A1 * | 1/2006 | Gabbay | 424/422 |
| 2006/0020327 | A1 * | 1/2006 | Lashinski | A61B 17/0644 623/1.25 |
| 2006/0074484 | A1 | 4/2006 | Huber | |
| 2006/0122692 | A1 | 6/2006 | Gilad et al. | |
| 2006/0149360 | A1 | 7/2006 | Schwammenthal et al. | |
| 2006/0173532 | A1 | 8/2006 | Flagle et al. | |
| 2006/0178586 | A1 * | 8/2006 | Dobak, III | 600/508 |
| 2006/0178740 | A1 | 8/2006 | Stacchino et al. | |
| 2006/0206202 | A1 | 9/2006 | Bonhoeffer et al. | |
| 2006/0241744 | A1 | 10/2006 | Beith | |
| 2006/0241745 | A1 | 10/2006 | Solem | |
| 2006/0259088 | A1 * | 11/2006 | Pastore | A61N 1/056 607/9 |
| 2006/0259120 | A1 | 11/2006 | Vongphakdy et al. | |
| 2006/0259137 | A1 | 11/2006 | Artof et al. | |
| 2006/0265056 | A1 | 11/2006 | Nguyen et al. | |
| 2006/0276813 | A1 | 12/2006 | Greenberg | |
| 2007/0010876 | A1 | 1/2007 | Salahieh et al. | |
| 2007/0027534 | A1 | 2/2007 | Bergheim et al. | |
| 2007/0043435 | A1 | 2/2007 | Seguin et al. | |
| 2007/0055358 | A1 | 3/2007 | Krolik et al. | |
| 2007/0067029 | A1 | 3/2007 | Gabbay | |
| 2007/0093890 | A1 | 4/2007 | Eliasen et al. | |
| 2007/0100435 | A1 | 5/2007 | Case et al. | |
| 2007/0118210 | A1 | 5/2007 | Pinchuk | |
| 2007/0213813 | A1 | 9/2007 | Von Segesser et al. | |
| 2007/0233228 | A1 | 10/2007 | Eberhardt et al. | |
| 2007/0244545 | A1 | 10/2007 | Birdsall et al. | |
| 2007/0244552 | A1 | 10/2007 | Salahieh et al. | |
| 2007/0288087 | A1 | 12/2007 | Fearnot et al. | |
| 2008/0021336 | A1 * | 1/2008 | Dobak, III | 600/508 |
| 2008/0021552 | A1 | 1/2008 | Gabbay | |
| 2008/0039934 | A1 | 2/2008 | Styrc | |
| 2008/0071369 | A1 | 3/2008 | Tuval et al. | |
| 2008/0082164 | A1 | 4/2008 | Friedman | |
| 2008/0097595 | A1 | 4/2008 | Gabbay | |
| 2008/0114452 | A1 | 5/2008 | Gabbay | |
| 2008/0125853 | A1 | 5/2008 | Bailey et al. | |
| 2008/0140189 | A1 | 6/2008 | Nguyen et al. | |
| 2008/0146934 | A1 * | 6/2008 | Czygan et al. | 600/453 |
| 2008/0147183 | A1 | 6/2008 | Styrc | |
| 2008/0154355 | A1 | 6/2008 | Benichou et al. | |
| 2008/0154356 | A1 | 6/2008 | Obermiller et al. | |
| 2008/0243245 | A1 | 10/2008 | Thambar et al. | |
| 2008/0252293 | A1 * | 10/2008 | Lagae et al. | 324/318 |
| 2008/0255662 | A1 | 10/2008 | Stacchino et al. | |
| 2008/0262602 | A1 | 10/2008 | Wilk et al. | |

(56) References Cited

U.S. PATENT DOCUMENTS

| | | |
|---|---|---|
| 2008/0269879 A1 | 10/2008 | Sathe et al. |
| 2009/0088836 A1* | 4/2009 | Bishop .................. A61F 2/2418 623/2.1 |
| 2009/0112309 A1 | 4/2009 | Jaramillo et al. |
| 2009/0138079 A1 | 5/2009 | Tuval et al. |
| 2009/0270729 A1* | 10/2009 | Corbucci et al. ............. 600/438 |
| 2009/0292242 A1* | 11/2009 | Konishi ................... 604/103.05 |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0094209 A1* | 4/2010 | Drasler et al. ............. 604/95.04 |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0198346 A1 | 8/2010 | Keogh et al. |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249661 A1* | 9/2010 | Righini et al. ................ 600/587 |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0098602 A1* | 4/2011 | Campbell et al. ............ 600/587 |
| 2011/0208290 A1* | 8/2011 | Straubinger .......... A61F 2/2418 623/1.15 |
| 2012/0197141 A1* | 8/2012 | Vanney et al. ................ 600/505 |
| 2012/0253457 A1 | 10/2012 | Winston et al. |
| 2016/0000590 A1* | 1/2016 | Boyden .................. A61B 5/026 623/1.15 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A1 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2009/042196 A2 | 4/2009 |
| WO | 2010008548 A2 | 1/2010 |
| WO | 2010096176 A1 | 8/2010 |
| WO | 2010098857 A1 | 9/2010 |

OTHER PUBLICATIONS

Catheter-implanted prosthetic heart valves, Knudsen, L.L., et al., The International Journal of Artificial Organs, vol. 16, No. 5 1993, pp. 253-262.

Design U.S. Appl. No. 29/375,243, filed Sep. 20, 2010.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Percutaneous aortic valve replacement: resection before implantation, 836-840, Quaden, Rene et al., European J. of Cardio-thoracic Surgery, 27 (2005).

Ruiz, Carlos, Overview of PRE-CE Mark Transcatheter Aortic Valve Technologies, Euro PCR (powerpoint)—dated May 25, 2010?

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

\* cited by examiner

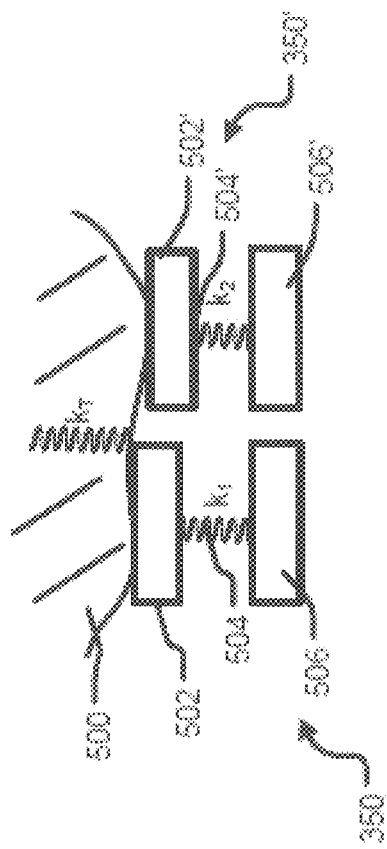
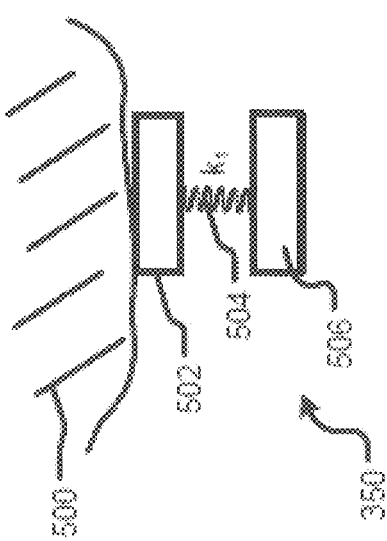

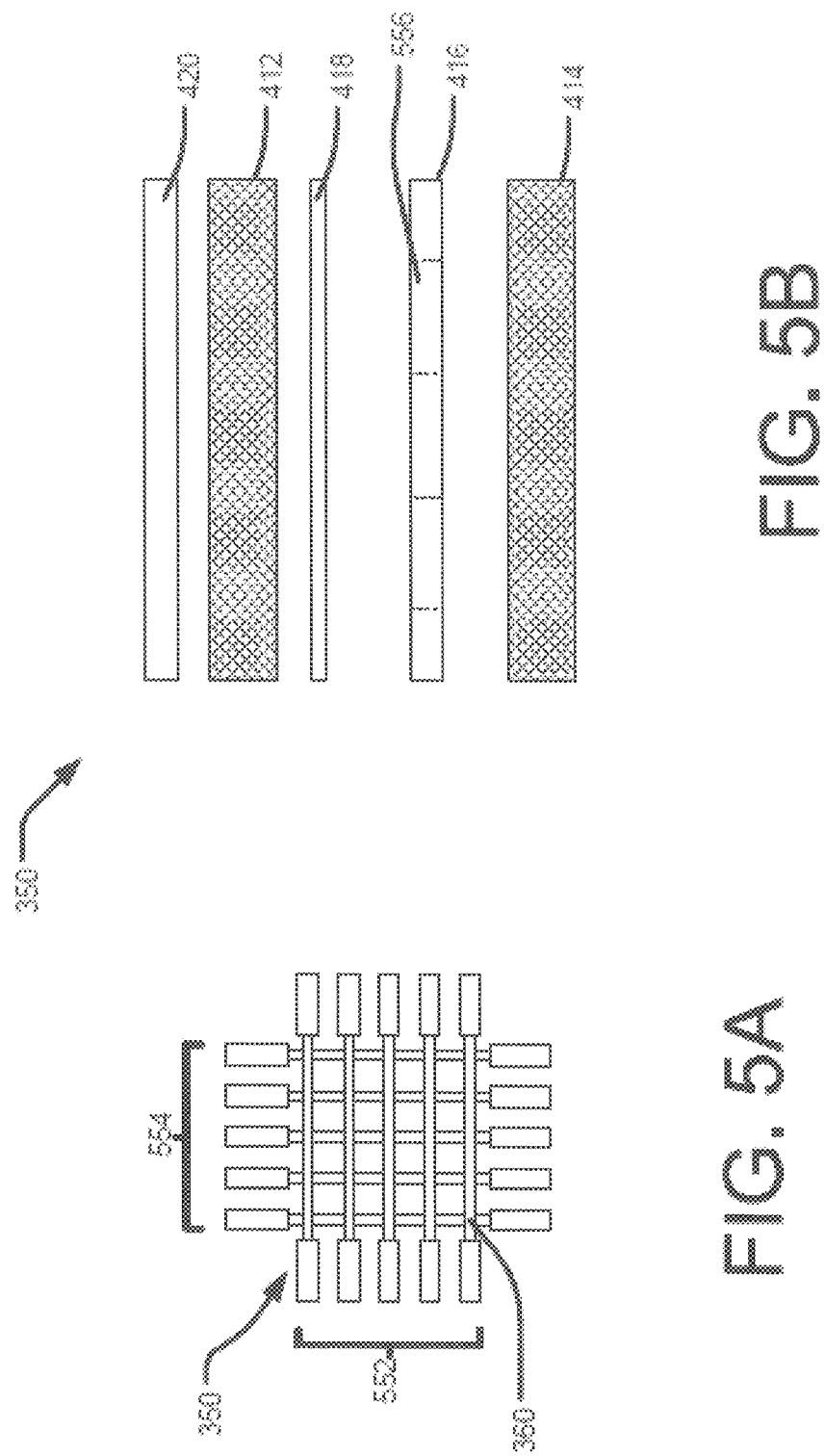

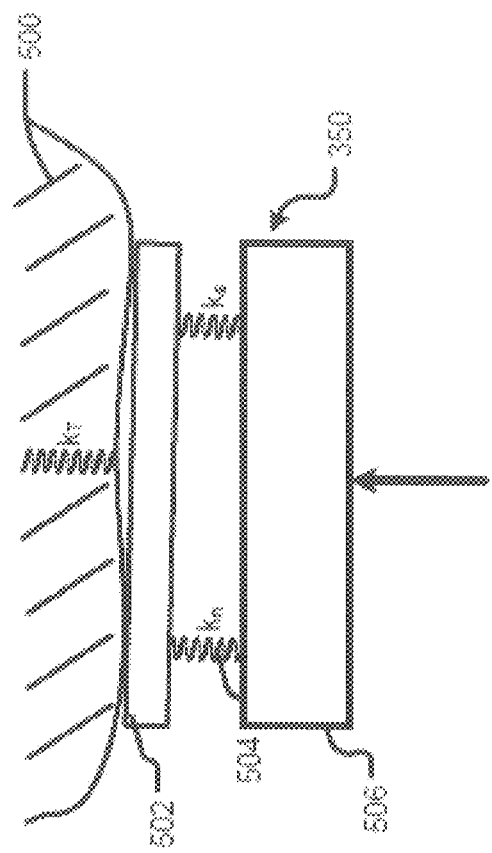
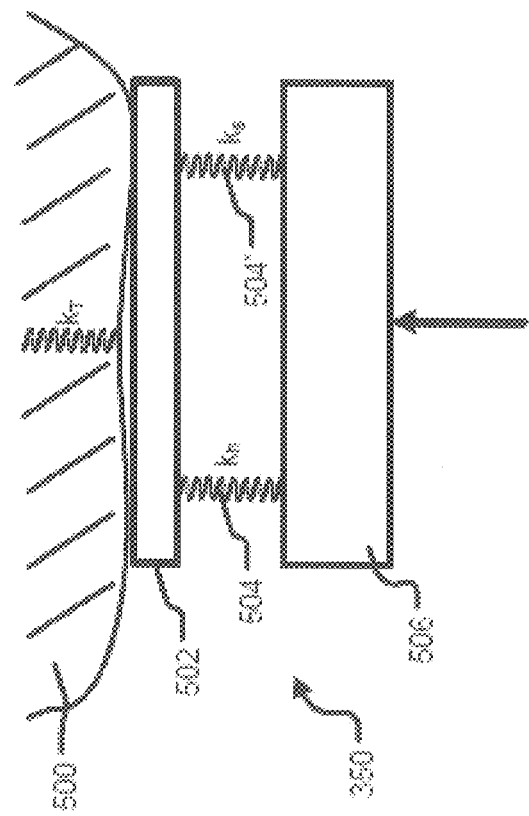
FIG. 5C

SIZING DEVICE AND METHOD OF POSITIONING A PROSTHETIC HEART VALVE

CROSS REFERENCE TO RELATED APPLICATION

The application claims the benefit of the filing date of U.S. Provisional Patent Application No. 61/713,171 filed Oct. 12, 2012, the disclosure of which is hereby incorporated herein by reference.

BACKGROUND OF THE INVENTION

The present invention relates to heart valve replacement and, in particular, to collapsible prosthetic heart valves. More particularly, the present invention relates to devices and methods for positioning and sizing collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in conventional delivery devices for self-expanding valves, the clinical success of the valve is dependent on accurate deployment and anchoring, and on acceptable valve performance both acutely and chronically. Inaccurate sizing and positioning increases risks, such as valve migration, which may result in severe complications due to obstruction of the left ventricular outflow tract and may even result in patient death. Additionally, calcification of the aortic valve may affect performance. Specifically, the degree of calcification has been suggested to play a role in anchoring transcathether implants. The interaction between the implanted valve and the calcified tissue of the aortic valve is believed to be relevant to anchoring the valve in place and preventing valve migration.

Without being bound to any particular theory, it is believed that improper anchoring of the valve may occur due to a mismatch between the size of the native annulus and the size of the prosthetic valve (e.g., using a small size valve in a large annulus), lower calcification levels in the native tissue than actually predicted, or improper positioning of the valve resulting in insufficient expansion of the valve diameter. Thus, methods and devices are desirable that would reduce the likelihood of valve migration caused by improper anchoring. In addition, incorrect sizing of a valve due to anatomical variations between patients may require removal of a fully deployed heart valve from the patient if it appears that the valve is not functioning properly. Removing a fully deployed heart valve increases the length of the procedure and increases the risk of infection and/or damage to heart tissue.

There therefore is a need for further improvements in the devices, systems, and methods for transcatheter delivery and positioning of collapsible prosthetic heart valves. Specifically, there is a need for further improvements in the devices, systems, and methods for accurately measuring the native annulus dimensions and calcification levels in a patient. Such accurate measurement will help to reduce the risks associated with valve migration and improper valve positioning. Among other advantages, the present invention may address one or more of these needs.

SUMMARY OF THE INVENTION

In some embodiments, a sizing device for use in implanting a collapsible prosthetic heart valve in a native valve annulus includes a collapsible and expandable stent having an annulus section and an aortic section and a sensor coupled to the annulus section of the stent, the sensor being capable of collecting information related to the native valve annulus.

In some examples, the stent may be self-expandable. The stent may include nitinol and the sensor may be flexible. The information may include the diameter of the native valve annulus. The information may include data relating to the extent of calcification of tissue of the native valve annulus. The sensor may include at least one capacitor having variable capacitance, the capacitance corresponding to the information. The sensor may include at least one piezoelectric material. The sensor may include a polymer, polymide, fabric or polydimethylsiloxane. The sensor may be a microelectromechanical sensor and may include at least two electrodes mounted on a fabric. The sizing device may further include deployment device configured to expand the collapsible and expandable stent via a series of rotations.

In some embodiments, a method for determining the proper fitment of a prosthetic heart valve within a native valve annulus includes (i) introducing a sizing device into the native valve annulus, the sizing device including (i) a collapsible and expandable stent having an annulus section and an aortic section and (ii) a sensor coupled to the annulus section of the stent, the sensor being capable of collecting information related to the native valve annulus, (ii) expanding the diameter of the stent within the native valve annulus and (iii) acquiring information related to the native valve annulus via the sensor.

In some examples, the information may include the diameter of the native valve annulus or data relating to an extent of calcification of tissue of the native valve annulus. The step of expanding the diameter of the stent may include rotating a first portion of a deployment device relative to a second portion of the deployment device within the native valve annulus. The stent may be self-expandable and the sizing device may further include a removable cannula disposed about the stent to maintain the stent in a collapsed configuration, and the step of expanding the diameter of the stent may include removing the cannula from around the stent.

In some examples, the method may further include expanding the diameter of the stent in-vitro to establish a relationship between the number of rotations of the first portion of the deployment device relative to the second portion of the deployment device and a diameter of the stent. The step of acquiring information related to the native valve annulus may include comparing the number of rotations within the native valve annulus to the relationship. The expanding step may include expanding the diameter of the stent within the native valve annulus until the sensor measures a radial force of predetermined value.

BRIEF DESCRIPTION OF THE DRAWINGS

Various embodiments of the present invention are disclosed herein with reference to the drawings, wherein:

FIG. 4A is a schematic view illustrating the principles of operation of a single microelectromechanical sensor;

FIG. 4B is a schematic view illustrating the principles of operation of multiple sensors;

FIG. 5A is a top plan view of a microelectromechanical sensor array in accordance with an embodiment of the present invention;

FIG. 5B is a close-up of a sensor structure of FIG. 5A with separated layers in accordance with an embodiment of the present invention;

FIG. 5C is a schematic view illustrating the principles of operation of a microelectromechanical sensor;

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
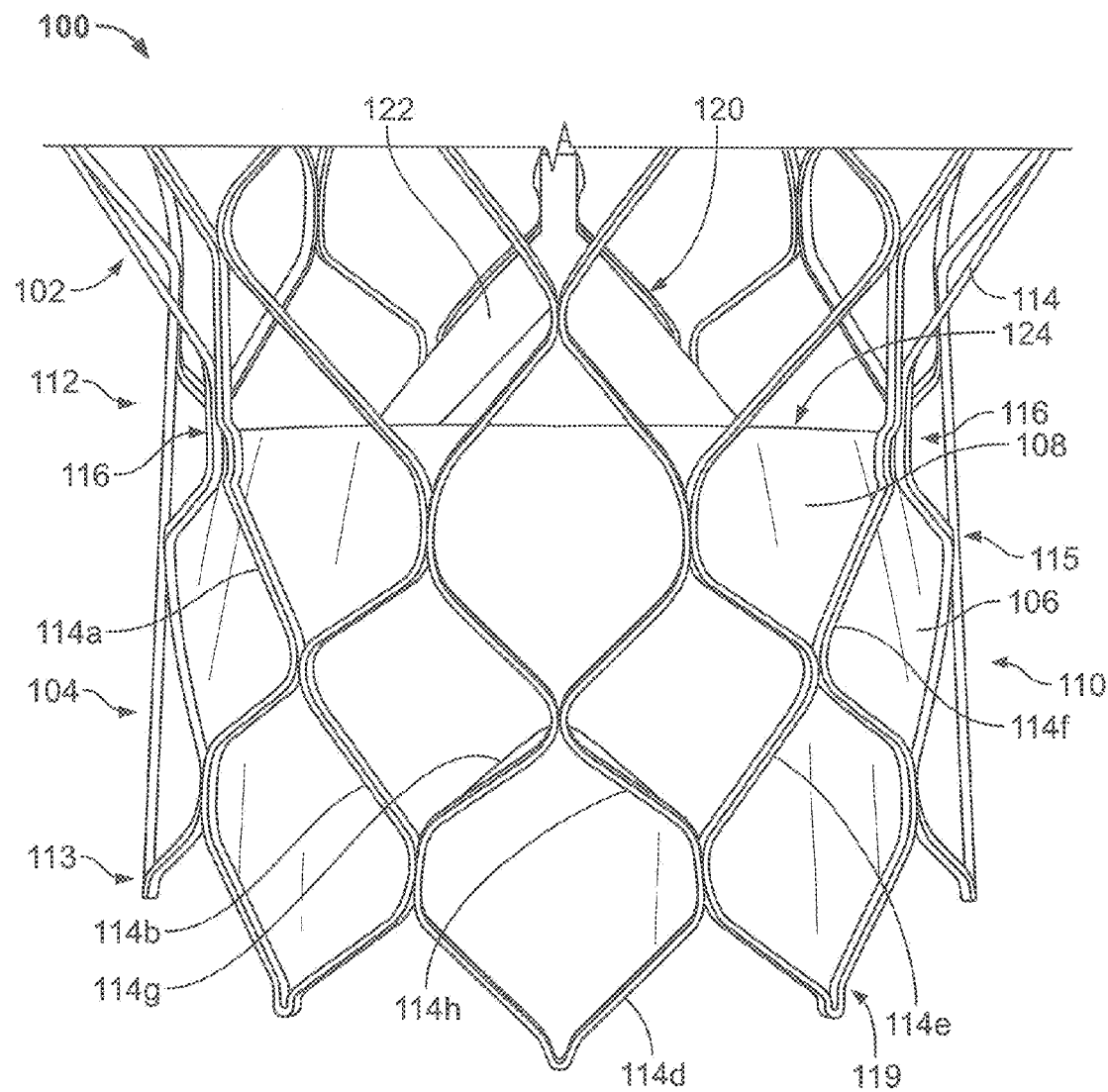
FIG. 1 is a side elevational view of a conventional prosthetic heart valve.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, an aortic section (not shown) and a transition section (not shown) disposed between the annulus section and the aortic section. Each of the annulus section 110, the aortic section and the transition section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features 116 connecting at least two cells 112 in the longitudinal direction of the stent 102. The commissure features 116 may include eyelets for facilitating the suturing of a valve assembly 104 to the sent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. The cuff 106 and/or the sutures used to attach the valve assembly 104 to stent 102 may be formed from or include ultra-high-molecular-weight polyethylene. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the cuff 106 or the stent 102 by any suitable attachment means, such as suturing, stapling, adhesives or the like. For example, the first edge 122 of each leaflet 108 may be bonded to the cuff 106, and the cuff may in turn be bonded to the stent 102. Alternatively, the first edge 122 of each leaflet 108 may be sutured to the stent 102 by passing strings or sutures through the cuff 106 of the valve assembly 104. A second or free edge 124 of each leaflet 108 may coapt with the corresponding free edges of the other leaflets, thereby enabling the leaflets to function collectively as a one-way valve.

Irrespective of the attachment means employed, the leaflets 108 may be attached to the cuff 106 or to the stent 102 along at least some struts 114 of the stent to enhance the structural integrity of the valve assembly 104. As a consequence of this attachment, the struts 114 help support the leaflets 108 of the valve assembly 104 and may therefore reduce the strain in the leaflet-cuff junction.

The leaflets 108 may be attached directly to and supported by certain struts 114, such as by suturing. In such event, the cuff 106 may perform little or no supportive function for the leaflets 108. Hence, the cuff 106 may not be subjected to high stresses and is therefore less likely to fail during use. In light of this, the thickness of the cuff may be reduced. Reducing the thickness of the cuff 106 results in a decrease in the volume of the valve assembly 104 in the collapsed condition. This decreased volume is desirable as it enables the prosthetic heart valve 100 to be implanted in a patient using a delivery device that is smaller in cross-section than conventional delivery devices. In addition, since the material forming the stent struts 114 is stronger than the material forming the cuff 106, the stent struts 114 may perform the supportive function for the leaflets 108 better than the cuff 106.

The volume of the valve assembly 104 may be further reduced by having the cuff 106 cover only a portion of the surface of annulus section 110. With continued reference to FIG. 1, the first or proximal end of the cuff 106 may substantially follow the contour of the first or proximal end 119 of the stent 102. As such, the proximal end of the cuff 106 may have a generally sinusoidal or zigzag shape. This eliminates any free edge of the cuff 106, which otherwise might extend directly between the cusps of the cells 112 at the proximal end 119 of the stent 102, and enables the entire length of the proximal end 118 of the cuff 106 to be secured to the stent 102. The second or distal end 120 of the cuff 106, on the other hand, may be disposed substantially along at least some struts 114, but not necessarily the struts in a single annular row of cells 112. More particularly, the distal end 120 of the cuff 106 may follow the stent struts 114 up to the commissure features 116, such that the cuff covers all of the cells 112 in the bottom annular row 113 of cells and in a second annular row 115 of cells located between the commissure features and the proximal end 119 of the stent 102, but covers a lesser area of cells in the annular regions between the commissure features. In other words, the distal end 120 of the cuff 106 may be disposed substantially along struts 114a, 114b, 114e, 114f, 114g and 114h, as shown in FIG. 1. Strut 114g may be connected at one end to strut 114h, and at the other end to the intersection of struts 114b and 114c. Strut 114h may be connected at one end to strut 114g, and at the other end to the intersection of struts 114d and 114e. Struts 114c, 114d, 114g, and 114h collectively form a single cell 112.

As a result of the foregoing configuration, all of the cells 112 in the bottom annular row 113 of cells may be entirely covered by the cuff 106. The cuff 106 may also entirely cover those cells 112 in the second annular row 115 that are located directly below the commissure features 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure features 116, there is little to no likelihood of leakage in the area of the cells between the commissure features in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

In operation, the embodiment of the prosthetic heart valve described above may be used to replace a native heart valve, such as the aortic valve. The prosthetic heart valve may be delivered to the desired site (e.g., near a native aortic annulus) using any suitable delivery device. Typically, during delivery, the prosthetic heart valve is disposed inside the delivery device in the collapsed condition. The delivery device may be introduced into a patient using a transfemoral, transapical, transseptal or other approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction. It will also be noted that while the inventions herein are predominantly described in terms of a tricuspid valve, the valve could be a bicuspid valve, such as the mitral valve, and the stent could have different shapes, such as a flared or conical annulus section, a less-bulbous aortic section, and the like, and a differently shaped transition section.

In certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency could not be treated well, if at all, with the current collapsible designs.

The reliance on evenly calcified leaflets could lead to several problems such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, the optimal valve would seal and anchor adequately without the need for excessive radial force, protrusion into the left ventricular outflow tract (LVOT), etc., that could harm nearby anatomy and physiology.

Figure 2A:
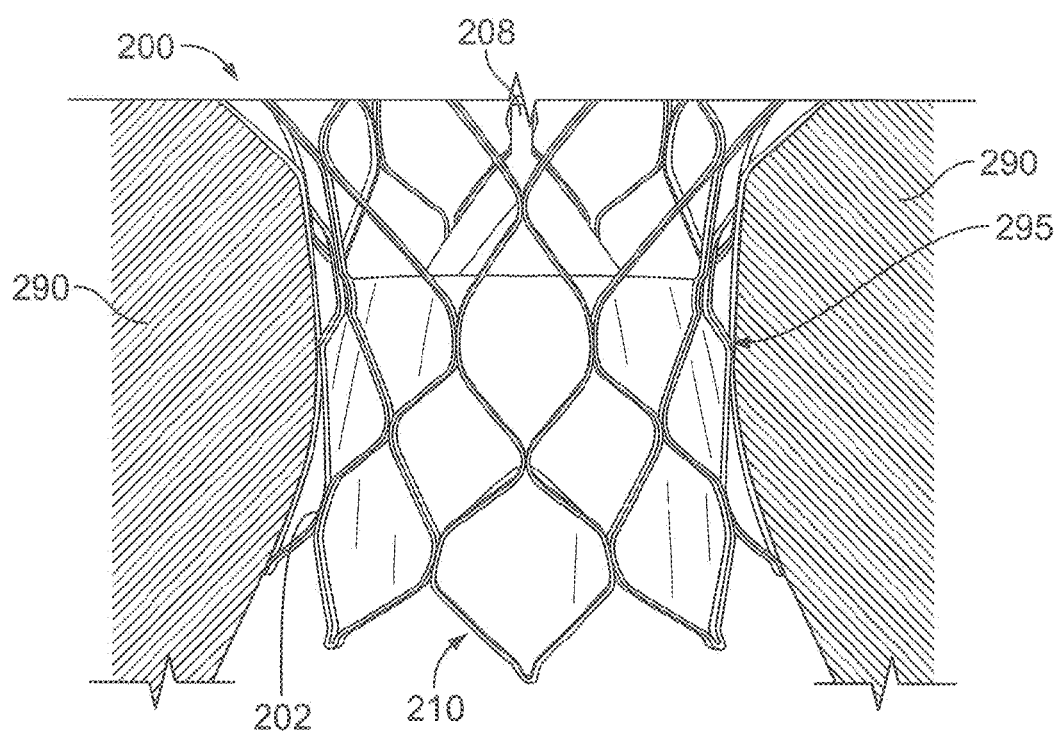
FIG. 2A is a side elevational view of a prosthetic heart valve having poor fitment.

FIG. 2A illustrates a prosthetic heart valve 200 positioned within the native valve annulus, the heart valve 200 having poor fitment. Specifically, as seen in FIG. 2A, the annulus section 210 of the stent 202 is distorted at portion 295 due to improper fitment of the stent 202 within annulus 290. Improper fitment of the prosthetic heart valve 200 may lead to improper valve function, as well as any of the problems discussed above. For example, as the stent 202 of a collapsible prosthetic heart valve 200 distorts during implantation, during beating of the heart, or because of irregularities in the patient's anatomy or the condition of the native valve, such distortion may be translated to the valve assembly 204, such that not all of the valve leaflets 208 meet to form effective coaptation junctions. This can result in leakage or regurgitation and other inefficiencies which can reduce cardiac performance. Moreover, if the prosthetic valve 200 is not placed optimally and the valve leaflets 208 are not coapting as intended, other long term effects, such as uneven wear of the individual leaflets 208, can be postulated. Such improper fitment may be due to poor positioning, disregard for calcification or due to use of the wrong valve size.

Figure 2B:
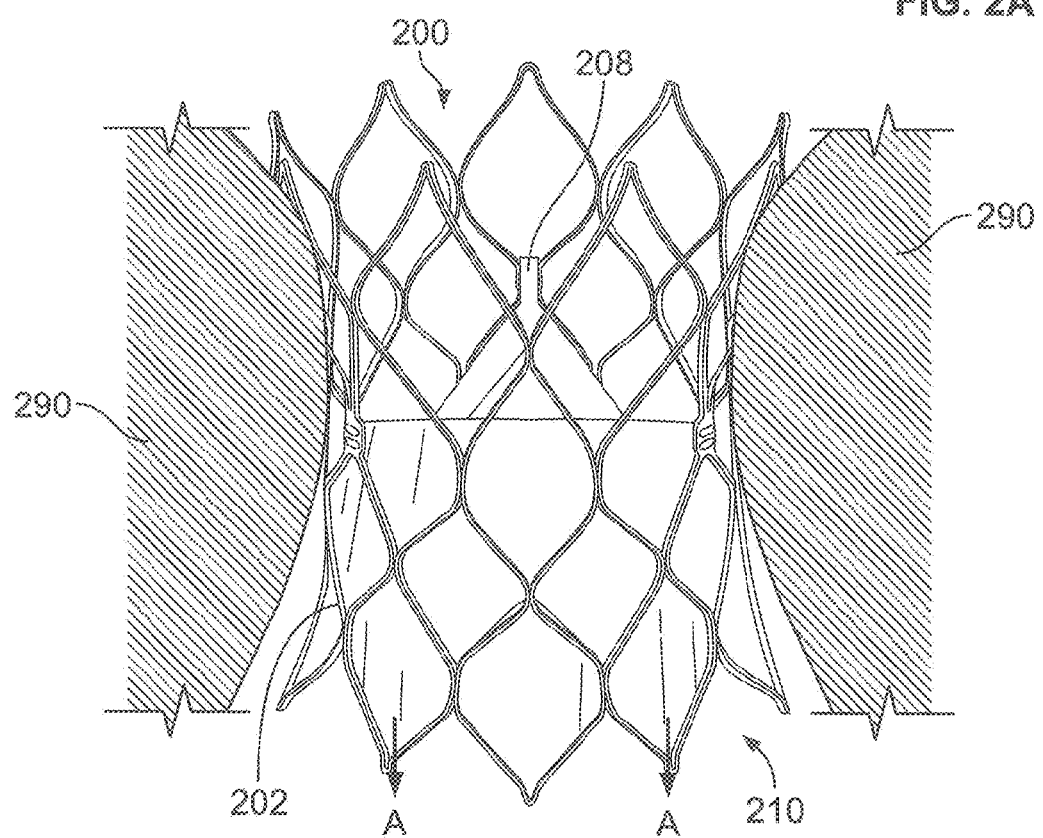
FIG. 2B is a side elevational view of a prosthetic heart valve that has improperly migrated.

Poor positioning, disregard for calcification or the use of the wrong valve size may also cause heart valve migration. As seen in FIG. 2B, prosthetic heart valve 200 has partially translated into the ventricle from its intended location within native valve annulus 290 as indicated by arrows "A", a condition that may lead to a host of problems as discussed above. Even a small shift in position, such as that seen in FIG. 2B, may cause inadequate sealing and improper valve function. Migration may also result in regurgitation of blood passing through the valve.

In order to avoid these problems, a valve sizing device may be used to accurately determine the annulus diameter and the calcification levels in the aortic valve. The valve sizing device may be first deployed within the native valve annulus to determine the shape and condition of the annulus. After obtaining sufficient measurements, the valve sizing device may be removed from the native valve annulus and a suitable prosthetic heart valve may be chosen based on the obtained measurements. The selected prosthetic heart valve may then be implanted, reducing the risk of deformation and/or migration.

Figure 3:
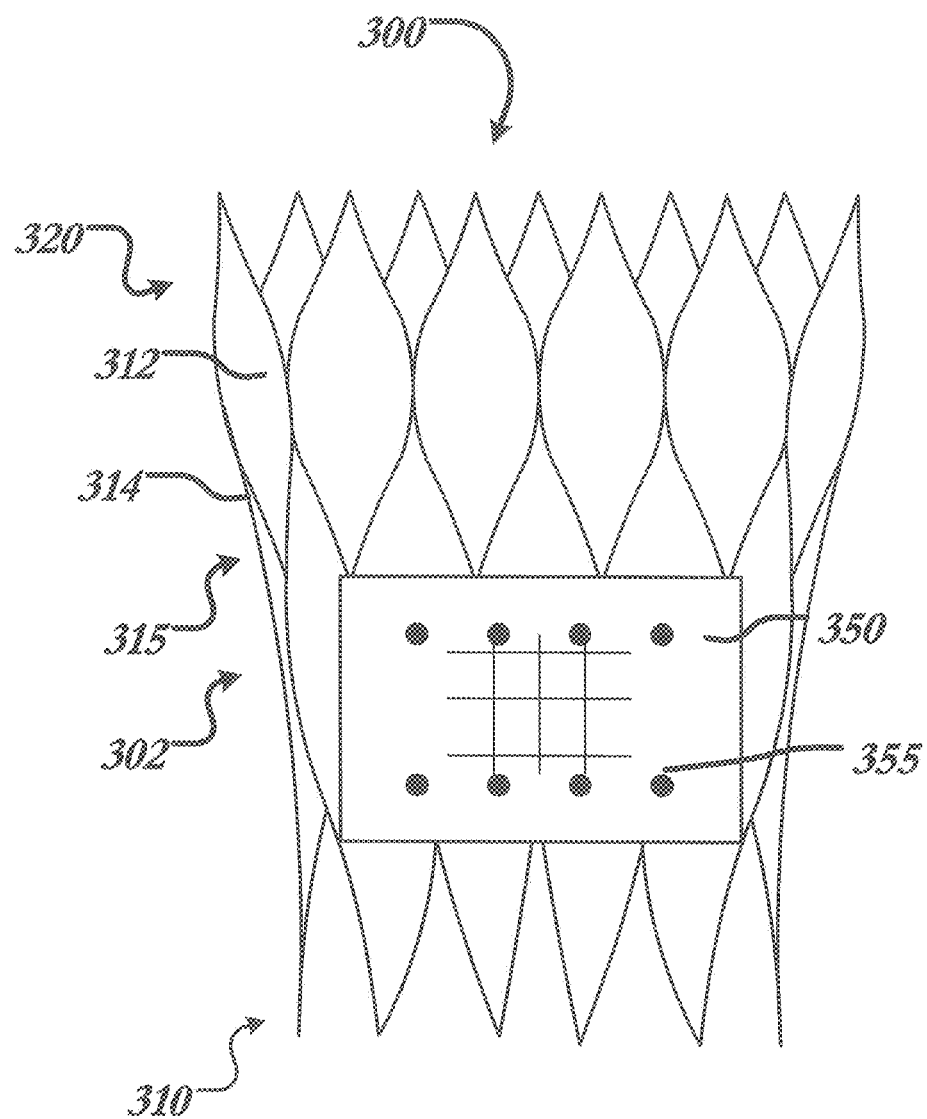
FIG. 3 is a side elevational view of a self-expandable nitinol stent having a microelectromechanical sensor according to one embodiment of the present invention.

FIG. 3 illustrates a valve sizing device 300 according to one embodiment of the present invention. The valve sizing device 300 includes a self-expandable stent 302 similar to stent 102 described above, and may be made from the same materials. The stent 302 may have an annulus section 310, an aortic section 320, and a transition section 315 disposed between the annulus section and the aortic section. Each of the annulus section 310, the aortic section 320 and the transition section 315 of the stent 302 includes a plurality of cells 312 connected to one another around the stent. The annulus section 310 and the aortic section of the stent 302 may include one or more annular rows of cells 312 connected to one another. For example, the annulus section 310 may have two annular rows of cells 312. When the sizing device 300 is in the expanded condition, each cell 312 may be substantially diamond shaped. Regardless of its shape, each cell 312 is formed by a plurality of struts 314. A cell 312 may be formed by four struts 314, for example.

As seen in FIG. 3, the valve sizing device 300 may further include a sensor 350 coupled to stent 302. Sensor 350 may be a microelectromechanical sensor and may include, but is not limited to, sensors capable of measuring capacitance between two electrodes. In some examples, sensors 350 may include piezoelectric sensors, optical sensors, electromagnetic sensors, capacitive sensors and the like positioned around the stent to measure a force applied to the sensor by the native valve annulus. By way of example, a FLEXIFORCE® sensor made by TEKSCAN® may be used to measure force.

Sensor 350 may be embedded within stent 302 or coupled to struts 314 of stent 302 in any suitable manner. For example, as seen in FIG. 3, sensor 350 may be coupled to struts 314 at various attachment points 355 around the perimeter of the stent. Thus, deformation of stent 302 also causes a corresponding deformation of sensor 350, and the sensor is assumed to comply with the intravascular geometry. It will be understood that more than one sensor 350 may be coupled to stent 302. For example, two or three sensors 350 may be evenly disposed about the circumference of stent 302. The sensors 350 may be disposed on the periphery of stent 302 so that they are capable of being in direct contact with body tissue.

By inserting sizing device within a native valve annulus, the radial force against the sensors may be measured. FIG. 4A illustrates use of a force sensor according to this embodiment. Though FIG. 4A illustrates a sensor having a spring, this example is merely illustrative and it will be understood that the sensor may be any of those described above as well as other sensors known in the art. A sensor 350 may include a contacting member 502, a spring 504 and a base layer 506. Spring 504 may be connected to both the contacting member 502 and the base layer 506 and disposed between the two. The sensor 350 may be positioned near target tissue 500 and, as can be appreciated from FIG. 4A, brought in contact with tissue 500, with contacting member 502 abutting the tissue. As the sensor 350 is gradually advanced, spring 504 begins to compress. Knowing the spring constant kl of spring 504, the force against contacting member 502 may be measured.

This measured radial force may be compared against values in a lookup table or database that provides adequate radial force for valves of varying diameter. These values may be obtained by in vitro testing. In at least some examples, the table or database may also include information relating to blood pressure to adjust for variations in blood pressure. Specifically, patients with higher blood pressure (e.g., 200 mm Hg) may suggest the need for greater radial forces for adequate anchoring while patients with lower blood pressure (e.g., 100 mm Hg or less) may call for lower radial forces.

In a second embodiment, multiple sensors may be located near one another to acquire information relating to elasticity of the surrounding tissue. FIG. 4B shows the concept of using a sensor 350 to measure calcification of tissue by measuring the tissue elasticity. A sensor 350 may include a contacting member 502, a spring 504 and a base layer 506. A second sensor 350 may include a contacting member 502', a spring 504' and a base layer 506'. Each spring 504,504' may be connected to its respective contacting member 502,502' and base layer 506,506' and disposed between the two. Moreover, sensors 350,350' may be positioned near target tissue 500 and, as can be appreciated from FIG. 4B, brought in contact with tissue 500, with contacting members 502,502' abutting the tissue. As the sensors 350,350' are gradually advanced, springs 504 and 504' begin to compress.

Springs 504 and 504' may have different spring constants. As shown in FIG. 4B, spring 504 has a spring constant of kl and spring 504' has a spring constant of $k_2$. Additionally, the stiffness of tissue 500 may be represented by a spring having a spring constant $k_T$. By pushing contacting members 502, 502' against tissue 500, the springs 504 and 504' will have different amounts of deflection based on the different spring constants. Specifically, spring 504' having a lower spring constant will suffer a greater deflection compared to its counterpart as shown in the figure on the right. The relative deflection of the springs may then be used to calculate the tissue stiffness represented by $k_2$. This may then be used to analyze the extent of calcification of the tissue and, to decalcify the tissue to a suitable level and to choose the appropriate prosthetic heart valve for implanting in the patient. Thus, by examining the force exerted on springs 504 and 504' and the displacement of both springs, the stiffness of tissue 500 may be determined. The stiffness of the tissue may then be used to select the appropriate valve or appropriate level of calcification needed as will be described in greater detail with reference to the algorithms and methods below.

In a third embodiment, microelectromechanical sensors may be used to measure the extent of calcification of a tissue. Details of these sensors will be fully discussed with reference to FIGS. 5A-E. In this embodiment, sensor 350 may be a microelectromechanical sensor and may include, but is not limited to, sensors capable of measuring capacitance, piezoelectricity or any other suitable parameter. Sensor 350 may also include a flexible tactile microelectromechanical sensor. One example of such sensor is known in the art and described in "Flexible Tactile Sensor For Tissue Elasticity Measurements," Journal of Microelectromechanical Systems, Vol. 19, No. 6, December 2009, the contents of which are hereby incorporated in its entirety as if fully recited herein.

FIGS. 5A and 5B illustrate one possible configuration of a suitable microelectromechanical sensor 350. Sensor 350 may be flexible and deformable in order to collect information about size, shape and calcification of the native aortic valve. In that regard, sensor 350 may be fashioned from fabric or flexible polymer layers such as polydimethylsiloxane (PDMS) or a polyimide having capacitors.

In one example, PDMS may be chosen as the structural material due to its advantageous properties such as flexibility, ductility, and biocompatibility. The biological and medical compatibility of the material has been well documented. Moreover, PDMS devices can be readily sterilized for medical applications. In addition, PDMS is mechanically much softer than other polymer materials commonly utilized in microfabrication.

Figure 5D:
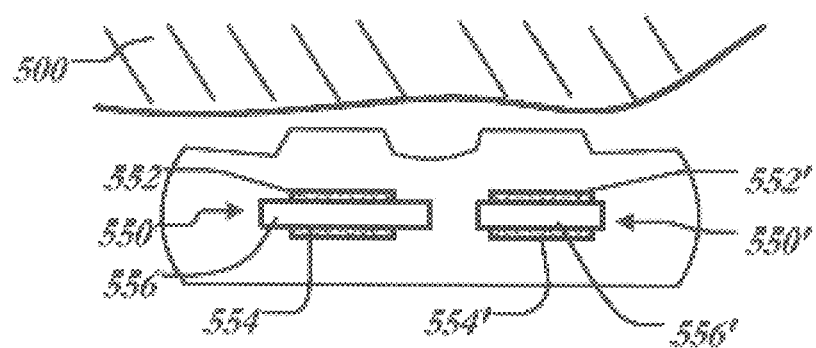
FIGS. 5D and 5E are schematic views illustrating a microelectromechanical sensor formed of a capacitative pair.

FIG. 5A illustrates a PDMS sensor array consisting of 5×5 capacitors 360, the operation of which will be described in greater detail with reference to FIGS. 5D and 5E. In order to minimize the wiring interfaces, the top and bottom electrodes may be oriented in orthogonal directions.

As seen in FIG. 5A, the intersection of wires forms each capacitor 360. A close-up of the sensor structure with separated layers is shown in FIG. 5B. Embedded electrodes are built on a top PDMS layer 412 and a bottom PDMS layer 414. A spacer layer 416 is sandwiched between the electrodes and defines air gaps 556. An insulation layer 418 may also be used to prevent the shorting of electrodes which could be the consequence when large deflection of sensing diaphragms occurs. Finally, a bump layer 420 is utilized to transfer contact forces through the air gap to be measured by capacitive change.

In order to illustrate the principle of operation of the invention, FIG. 5C shows the concept of using a sensor 350 to measure calcification of tissue by measuring the tissue elasticity. A sensor 350 may include a contacting member 502, a pair of springs 504 and 504' and a base layer 506. Springs 504 and 504' may be connected to both the contacting member 502 and the base layer 506 and disposed between the two. The sensor 350 may be positioned near target tissue 500 and, as can be appreciated from FIG. 5C, brought in contact with tissue 500, with contacting member 502 abutting the tissue. As the sensor 350 is gradually advanced, springs 504 and 504' begin to compress.

Springs 504 and 504' may have different spring constants. As shown in FIG. 5C, spring 504 has a spring constant of kh and spring 504' has a spring constant of $k_S$. Additionally, the stiffness of tissue 500 may be represented by a spring having a spring constant $k_T$. By pushing contacting member 502 against tissue 500, the springs 504 and 504' will have different amounts of deflection based on the different spring constants. Specifically, spring 504' having a lower spring constant will suffer a greater deflection compared to its counterpart as shown in the figure on the right. The relative deflection of the springs may then be used to calculate the tissue stiffness represented by $k_T$. This may then be used to analyze the extent of calcification of the tissue and, to decalcify the tissue to a suitable level and to choose the appropriate prosthetic heart valve for implanting in the patient. Thus, by examining the force exerted on springs 504 and 504' and the displacement of both springs, the stiffness of tissue 500 may be determined.

Figure 5E:
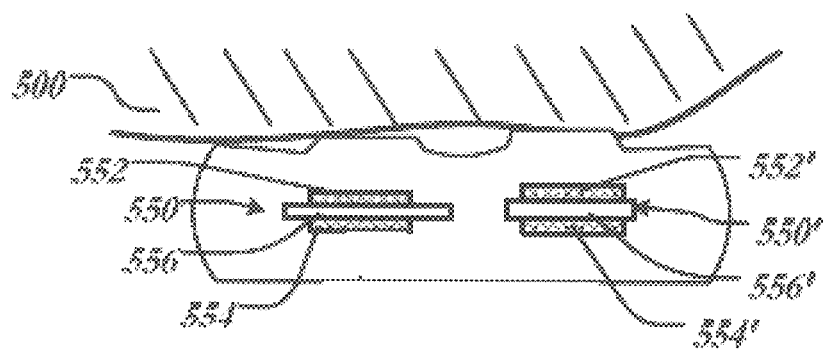

In one embodiment of implementing this concept, a capacitor pair for the sensors 350 may be used, as shown in FIGS. 5D and 5E. As shown in these figures, capacitor 550 includes a first top electrode 552, a first bottom electrode 554 and a first air gap 556 to form a first capacitor. A second capacitor is formed of a second top electrode 552', a second bottom electrode 554' and a second air gap 556' disposed between the second top electrode and the second bottom electrode. As seen in FIG. 5D, air gaps 556 and 556' are formed of varying areas analogous to the different springs discussed above with reference to FIG. 5C. When the sensor is contacted by tissue 500 as seen in FIG. 5D, relative deflection may be precisely measured by the capacitive change of each element as shown in FIG. 5E. The ratio of deflection (based on the capacitive change of each capacitor) may then be compared against valves in tables or graphs of known relationships between deflection change ratios and tissue stiffness to classify the tissue stiffness and determine the presence and degree of calcification.

Figure 6A:
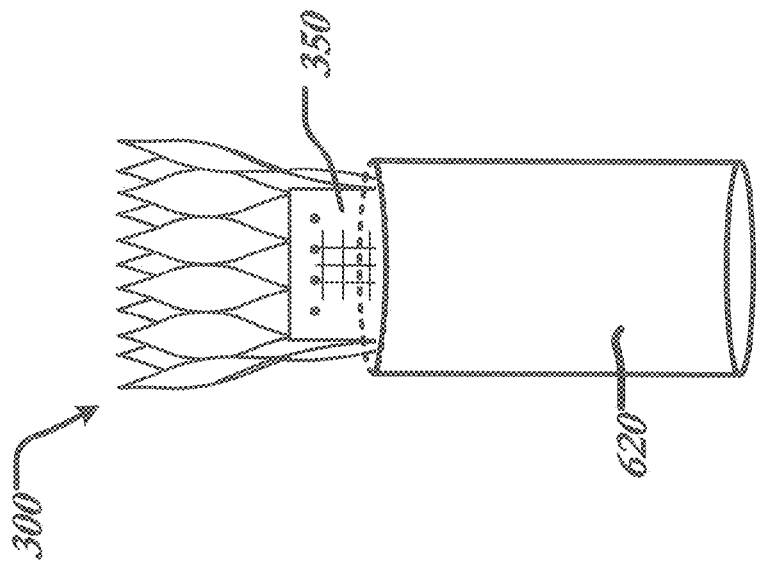
FIG. 6A is a side elevational view of a sizing device having a microelectromechanical sensor coupled to an inner deployment device.

FIG. 6A is a side elevational view of a sizing device 300 having a microelectromechanical sensor 350. A deployment device 610 for deploying sizing device 300 may be disposed inside the annulus section of the sizing device and may be coupled to the struts of the sizing device. Actuating the deployment device 610 may serve to gradually expand the sizing device 300. For example, rotating a first portion of the deployment device 610 in a first direction relative to a second portion thereof may expand the sizing device 300, while rotating the first portion of the deployment device relative to the second portion in a second direction, counter to the first, may collapse the sizing device 300.

Figure 6B:
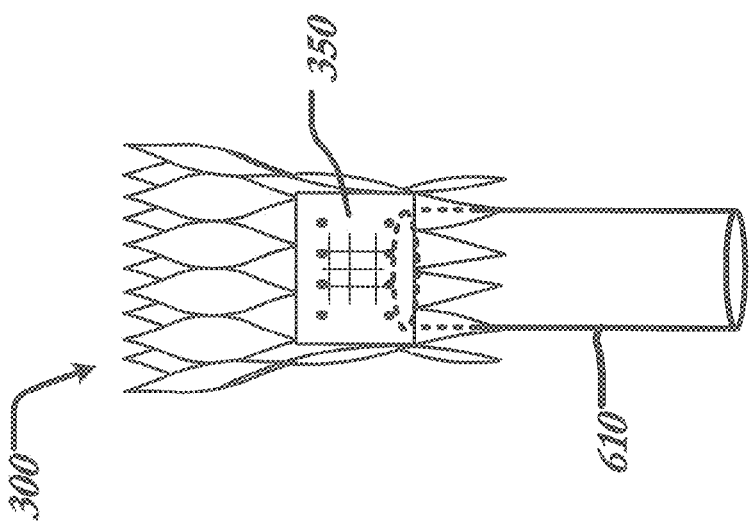
FIG. 6B is a side elevational view of a sizing device having a microelectromechanical sensor coupled to an outer deployment device.

FIG. 6B is a side elevational view of a sizing device 300 having a microelectromechanical sensor 350, with the sizing device coupled to an outer deployment device 620. In contrast to the "inner" deployment device 610 described above, the "outer" deployment device is disposed on the outside of the annulus section of the sizing device 300, and may be coupled to the struts 314 thereof. Like inner deployment device 610, outer deployment device 620 serves to gradually expand the sizing device 300. This may be accomplished by rotating two portions of the delivery device 620 relative to one another, as with the delivery device 610. Alternatively, outer deployment device 620 may be configured as a sheath that progressively exposes the sizing device 300. In examples in which sizing device 300 includes a self-expandable stent 302, as the sizing device is unsheathed from outer deployment device 620, the stent is able to expand to its maximal diameter.

Figure 7:
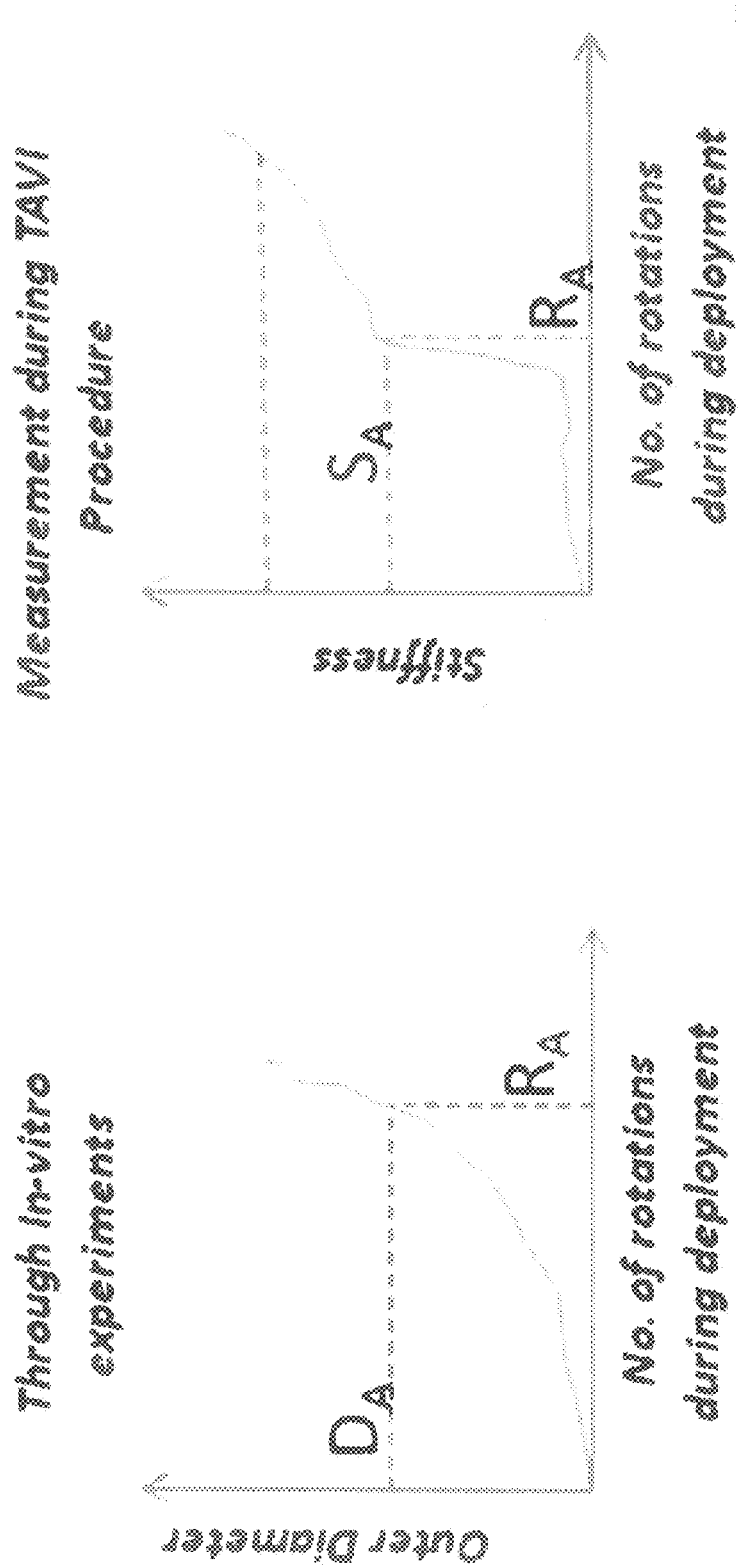
FIG. 7 is a pair of graphs showing the use of data from a microelectromechanical sensor in estimating annulus diameter and calcification levels.

FIG. 7 shows the use of data from a microelectromechanical sensor 350 in estimating annulus diameter and calcification levels. The diameter of the annulus may be estimated using a three-step process.

The graph on the left illustrates the first step in this process. In the first step, the sizing device 300 is expanded in-vitro using a deployment device, such as one of the deployment devices described above with reference to FIGS. 6A and 6B. Regardless of the deployment device used, it may include a rotating mechanism for gradually expanding the sizing device 300. A plot of the number of rotations of the deployment device and the outer diameter of the sizing device 300 may be formed to illustrate the relationship between the two. For example, by examining the plot of FIG. 7, at number of rotations $R_A$, the outer diameter is determined to be $D_A$.

In a second step, the sizing device 300 may be collapsed and inserted into the patient body at the target size. Using the same deployment device of the first step, the sizing device 300 may be gradually expanded. As the device expands, measurements of the force against the sensor 350 may be collected and the stiffness of the tissue calculated. The user may stop expanding the sizing device 300 once the measured force is had reached a predetermined value. The calculated stiffness may then be plotted against the number of rotations of the deployment device. As seen in FIG. 7, a steep increase in stiffness to stiffness $S_A$ appears at $R_A$ rotations of the deployment device. This sudden increase in stiffness indicates to the user that the sensor 350 has been brought into contact with tissue 500.

In a third step, the two graphs can be compared and the information may in turn be used to determine the appropriate size and/or shape of the prosthetic heart valve to be implanted. Specifically, the user may identify the number of rotations $R_A$ at which stiffness increased and compare this to the in-vitro experiment. By identifying the same number of rotations $R_A$ in the in-vitro step (the first graph), the corresponding outer diameter $D_A$ of the sizing device 300 may be obtained and the appropriate size and shape of the prosthetic heart valve chosen. It will be understood that this technique of measurement and comparison may be done with multiple sensors 350, each sensor 350 collecting data at various locations within the annulus of the valve. With enough data points, the desired shape and size of the prosthetic heart valve may be determined.

To use the sizing device 300 for sizing, positioning and selecting an appropriate prosthetic heart valve, the sizing device 300 may be deployed in-vitro using a deployment device to establish the relationship between rotations of a component of the deployment device during deployment and the outer diameter of the sizing device.

The sizing device 300 may then be collapsed and inserted into the patient transfemorally or transapically and advanced to the desired site for valve replacement. That is, the sizing device 300 may be advanced from the femoral vein through the iliac vein, the inferior vena cava, and the right atrium until reaching the deployment site, which will depend on the valve being replaced. This route requires the least amount of bending or turning. Minimizing the number of turns may facilitate control of the sizing device 300. If the sizing device 300 includes echogenic materials, it may be guided to the appropriate position using the assistance of three-dimensional echocaradiography to visualize the sizing device within the patient.

Once sizing device 300 has reached the desired site of measurement, it may be unsheathed or otherwise deployed using the deployment device to assume its fully expanded shape. With the sizing device 300 in its expanded condition, measurements relating to the tissue stiffness and thus, calcification, may be taken using sensor 350. After sufficient data has been collected, the sizing device 300 may be resheathed or otherwise collapsed and removed from the patient's body.

The collected data and the in-vitro data may then be used to select the appropriate valve size. A suitable prosthetic heart valve may be chosen, deployed and anchored at the desired site using any technique known in the art.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A sizing device for use in implanting a collapsible prosthetic heart valve in a native valve annulus, the sizing device comprising:
   a collapsible and expandable stent having an annulus section at a first end with a first diameter and an aortic section at a second end with a second diameter, the second diameter being greater than the first diameter, and the first end and the second end being disposed at opposite sides of the stent; and
   a sensor coupled to the annulus section adjacent the first diameter of the stent, the sensor comprising at least one deflectable contacting member, and being capable of collecting information related to stiffness of the native valve annulus by contacting portions of the native valve annulus with the at least one deflectable contacting member.

2. The device of claim 1, wherein the stent is self-expandable.

3. The device of claim 2, wherein the stent comprises nitinol.

4. The device of claim 2, wherein the sensor is flexible.

5. The device of claim 1, wherein the information includes the diameter of the native valve annulus.

6. The device of claim 1, wherein the information includes data relating to the extent of calcification of tissue of the native valve annulus.

7. The device of claim 1, wherein the sensor includes at least one capacitor having variable capacitance, the capacitance corresponding to the information.

8. The device of claim 1, wherein the sensor includes at least one piezoelectric material.

9. The device of claim 1, wherein the sensor comprises a polymer.

10. The device of claim 9, wherein the polymer comprises polydimethylsiloxane.

11. The device of claim 1, wherein the sensor is a microelectromechanical sensor.

12. The device of claim 1, wherein the sensor comprises at least two electrodes mounted on a fabric.

13. The device of claim 1, further comprising a deployment device configured to expand the collapsible and expandable stent via a series of rotations.

14. A method for determining the fitment of a prosthetic heart valve within a native valve annulus, comprising:

introducing a sizing device into the native valve annulus, the sizing device including (i) a collapsible and expandable stent having an annulus section at a first end with a first diameter and an aortic section at a second end with a second diameter, the second diameter being greater than the first diameter, and the first end and the second end being disposed at opposite sides of the stent and (ii) a sensor coupled to the annulus section of the stent, the sensor comprising at least one deflectable contacting member, and being capable of collecting information related to the native valve annulus by contacting portions of the native valve annulus with the at least one deflectable contacting member;

expanding the diameter of the stent within the native valve annulus; and acquiring information related to the native valve annulus via the sensor by contacting portions of the native valve annulus with the at least one deflectable contacting member of the sensor.

15. The method of claim 14, wherein the information includes the diameter of the native valve annulus.

16. The method of claim 14, wherein the information includes data relating to an extent of calcification of tissue of the native valve annulus.

17. The method of claim 14, wherein the step of expanding the diameter of the stent includes rotating a first portion of a deployment device relative to a second portion of the deployment device within the native valve annulus.

18. The method of claim 14, wherein the stent is self-expandable, the sizing device further includes a removable cannula disposed about the stent to maintain the stent in a collapsed configuration, and the step of expanding the diameter of the stent includes removing the cannula from around the stent.

19. A method for determining the fitment of a prosthetic heart valve within a native valve annulus, comprising:

introducing a sizing device into the native valve annulus, the sizing device including (i) a collapsible and expandable stent having an annulus section and an aortic section, and (ii) a sensor coupled to the annulus section of the stent, the sensor comprising at least one deflectable contacting member, and being capable of collecting information related to the native valve annulus by contacting portions of the native valve annulus with the at least one deflectable contacting member;

expanding the diameter of the stent within the native valve annulus by rotating a first portion of a deployment device relative to a second portion of the deployment device within the native valve annulus;

acquiring information related to the native valve annulus via the sensor by contacting portions of the native valve annulus with the at least one deflectable contacting member of the sensor; and expanding the diameter of the stent in-vitro to establish a relationship between the number of rotations of the first portion of the deployment device relative to the second portion of the deployment device and a diameter of the stent.

20. The method of claim 19, wherein the step of acquiring information related to the native valve annulus includes comparing the number of rotations within the native valve annulus to the relationship.

21. A method for determining the fitment of a prosthetic heart valve within a native valve annulus, comprising:

introducing a sizing device into the native valve annulus, the sizing device including (i) a collapsible and expandable stent having an annulus section and an aortic section and at least two diameters and (ii) a sensor coupled to the annulus section of the stent, the sensor comprising at least one deflectable contacting member, and being capable of collecting information related to the native valve annulus by contacting portions of the native valve annulus with the at least one deflectable contacting member;

acquiring information related to the native valve annulus via the sensor by contacting portions of the native valve annulus with the at least one deflectable contacting member of the sensor; and expanding the diameter of the stent within the native valve annulus by rotating a first portion of a deployment device relative to a second portion of the deployment device within the native valve annulus until the sensor measures a radial force of a predetermined value.

* * * * *